United States Patent [19]

Levine et al.

[11] Patent Number: 5,137,832

[45] Date of Patent: Aug. 11, 1992

[54] QUANTIFICATION OF FIBRINOGEN IN WHOLE BLOOD SAMPLES CONTAINED IN A TUBE USING A FLOAT TO SEPARATE MATERIALS

[75] Inventors: Robert A. Levine, Guilford; Stephen C. Wardlaw, Old Saybrook; Allan H. Hart, Guilford, all of Conn.

[73] Assignee: Becton Dickinson & Company, Franklin Lakes, N.J.

[21] Appl. No.: 636,677

[22] Filed: Jan. 2, 1991

[51] Int. Cl.$^5$ .................. G01N 31/02; G01N 33/86
[52] U.S. Cl. ................... 436/69; 73/61.1 R; 73/61.4; 73/64.1; 210/782; 436/70; 73/61.43; 73/61.63; 73/61.41
[58] Field of Search ............... 436/69, 70; 210/516, 210/782; 73/61.1 R, 61.4, 64.1, 149

[56] References Cited

U.S. PATENT DOCUMENTS

| | | | |
|---|---|---|---|
| 4,027,660 | 6/1977 | Wardlaw et al. | 73/149 X |
| 4,315,892 | 2/1982 | Stone et al. | 210/782 X |
| 4,443,345 | 4/1984 | Wells | 210/516 X |
| 4,567,754 | 2/1986 | Wardlaw et al. | 73/61.4 X |
| 4,818,418 | 4/1989 | Saunders | 210/782 |
| 4,954,264 | 9/1990 | Smith | 210/782 |

OTHER PUBLICATIONS

Millar et al., J. Clin. Path., vol. 24, pp. 827–830, 1971.
Millar et al., Chemical Abstracts, vol. 76, No. 23, Abstract No. 76:137699y, 1971.

*Primary Examiner*—Robert J. Hill, Jr.
*Attorney, Agent, or Firm*—William W. Jones

[57] ABSTRACT

Quantification of blood plasma fibrinogen content is made in a sample of anticoagulated whole blood contained in a sampling tube. The tube is a transparent centrifuge tube which contains a sample constituent layer-elongating float. The blood sample is centrifuged in the tube containing the float, and various cell constituent measurements are made. The centrifuged sample is then heated and recentrifuged to cause the precipitated fibrinogen to layer out on top of the float remote from the buffy coat band in the plasma layer. The thickness of the fibrinogen band is then measured, whereby quantification of the fibrinogen content of the blood sample can be made by a precalibrated instrument.

8 Claims, 1 Drawing Sheet

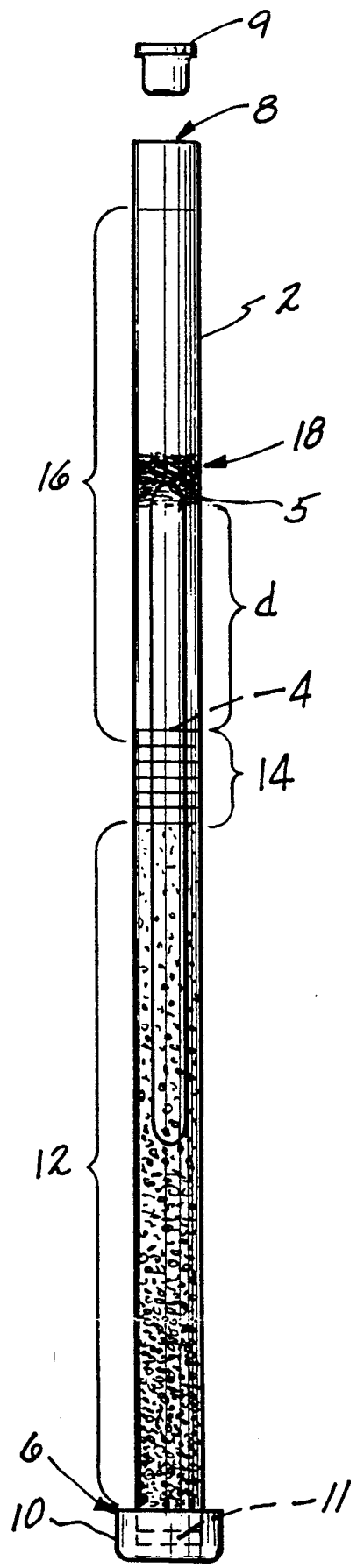

QUANTIFICATION OF FIBRINOGEN IN WHOLE BLOOD SAMPLES CONTAINED IN A TUBE USING A FLOAT TO SEPARATE MATERIALS

This invention relates to a procedure for quantifying blood fibrinogen content in blood samples. More particularly, this invention relates to a procedure for quickly and accurately visually determining the fibrinogen content in a centrifuged blood sample.

Fibrinogen is a major blood plasma protein that is necessary for proper blood clotting. The amount of fibrinogen present in the blood is directly proportional to the ability of the blood to form clots. Fibrinogen in the blood is transformed to fibrin during clot formation, thus fibrinogen deficiencies will result in inadequate fibrin formation and inadequate clotting.

Deficiencies in levels of fibrinogen in blood plasma can be caused by decreased fibrinogen production, which may result from liver failure, or from congenital hypofibrinogenemia. Disseminated intravascular coagulation of blood, a pathologic event, can also create a greater than normal consumption of fibrinogen available for use in clot formation. Obviously, fibrinogen deficiencies can result in excessive bleeding.

Excessive fibrinogen in the blood is also an anomalous condition which is generally associated with inflammatory states. High fibrinogen content in the blood can predispose a hypercoagulable state which is undesirable. Significantly elevated fibrinogen levels are also found in pregnant women.

It has also been determined that increases in fibrinogen concentrations in the blood are a risk factor for cardiovascular disease.

From the above, it is obvious that monitoring of the fibrinogen level in the blood is a useful procedure for determining the health of a patient, and can be used as a tool for preliminary indications of abnormal physical conditions. Blood fibrinogen content analysis is thus a valuable procedure to be used in normal patient check-ups or physicals as an early warning device.

There are several available methods for the quantitative measurement of blood plasma fibrinogen. The presently used methods require that the plasma be separated completely from the red blood cells, and most then require the conversion of the fibrinogen to fibrin in the separated plasma. The fibrin is then quantitated either gravimetrically; nephelometrically; or by chemical analysis. Immunologic and chemical/physical precipitation quantifications of the fibrinogen in the blood plasma are also disclosed in the prior art.

A procedure published in 1971 by Millar relates to the measurement of a heat precipitated fibrinogen band in a centrifuged blood plasma fraction. This heat precipitation of fibrinogen was as described in the Millar paper also described by others, including Fredericq in 1877; Schulz in 1955; Goodwin in 1965; and Low et al in 1967. After the plasma is separated from the remainder of the blood sample, the plasma is aspirated into a microhematocrit tube, and heated therein at a temperature of 56 degrees C. for three minutes in a water bath. The heated sample is then centrifuged so that a precipitated band of fibrin forms in the plasma. The amount of fibrinogen in the sample is then quantified by dividing the length of the fibrin band by the length of the original plasma column. This method converts the volume percentage of the packed precipitated fibrin directly into a fibrinogen concentration, and assumes that the packed fibrin volume in ml/100 ml of plasma is essentially one percent (1.0%) of the fibrinogen concentration in the blood sample expressed in mg/100 ml of blood. Using the aforesaid procedure, no fibrinogen will be found remaining in the supernatant plasma after heating and centrifugation. It has also been determined that none of the other normal plasma protein is precipitated by the heating step.

The aforesaid procedures, except for the Low et al procedure referenced above and described below, for quantifying fibrinogen in a blood sample are relatively complex and time-consuming since they all require that a whole blood sample be pretreated so that the plasma may be isolated from the other blood components, and then separated from the other blood components. The separated blood plasma must then be transferred to another container for further processing and analysis. The complexity of the total test protocol for measuring fibrinogen dictates that the analysis must be done in a medical testing laboratory, and is not likely to be performed in a physician's office.

The Low et al 1967 method, while avoiding the preliminary step of separating formed components of the blood from the plasma, does not separate the precipitated fibrinogen from the buffy coat, which also settles on top of the packed red blood cells. The Low et al method as described by Millar involves heating for three minutes at 56 degrees C. a previously centrifuged microhematocrit tube containing a blood sample. The tube is then re-spun in a centrifuge at 12,000 G for three minutes and the heat precipitated fibrinogen settles directly on the top of the similarly colored buffy coat.

This invention relates to a method for quantifying the fibrinogen content of a blood sample through a simple centrifugation protocol using a blood sample tube and float disclosed in the prior art for measuring white blood cell counts, amoung other things. The paraphenalia and general cell count measuring procedures used are disclosed in U.S. Pat. Nos. 4,027,660, granted Jun. 7, 1977; 4,077,396, granted Mar. 7, 1978; 4,082,085, granted Apr. 4, 1978; and 4,137,755 granted Feb. 6, 1979, which all are all specifically incorporated herein in their entireties. A number of additional patents have been granted to the inventors herein, which utilize the tube and float paraphenalia to perform other analyses of blood and other samples The method of this invention employs a transparent tube, such as a capillary tube, or the like, for containing the blood sample. A plastic float is disposed in the tube, and the blood sample is introduced into the tube which contains the float. Cell layer-enchancing stains are coated onto the tube bore wall. The blood sample is centrifuged as set forth in the above-identified prior art, and the white cell, hematocrit, and platelet counts are read. After the initial centrifugation and cell count ascertainments, the sample is heated to a temperature of about 56 degrees C. for about five minutes. This causes the fibrinogen to precipitate out in the plasma, whereafter a subsequent centrifugation step causes the fibrinogen precipitate to settle out on top of the float. The top of the float is offset from the top of the buffy coat a discernable distance so that the fibrinogen layer is clearly distinguishable from the buffy coat layer. The annular space between the float and the tube bore is sufficiently small so as to prevent the precipitated fibrinogen strands from settling therein. The fibrinogen band is thus clearly distinguishable, and also its axial length can be accurately measured in an appropriately modified instrument of the general type disclosed in U.S. Pat. Nos. 4,209,226, granted Jun. 24, 1980; and 4,558,947, granted Dec. 17, 1985. The instrument/microprocessor software need merely be modified so as to convert the fibrinogen layer axial length into a quantitative measurement of the fibrinogen content of the blood sample.

A conversion formula when a capillary tube is used has been ascertained by laboratory analysis of samples by the capillary tube procedure disclosed herein, and standard procedures, with the results of both being integrated. The conversion formula for use with a commercially available venous capillary tube sold by Becton Dickinson and Company under the trademark "QBC" capillary tube filled with 111 μl of blood is:

$$F_q = KF_l + b;$$

wherein:
- $F_q$ is the quantitated amount of fibrinogen in the blood in mg per dl;
- $F_l$ is the length of the precipitated fibrinogen band found in the tube at the top of the float measured in units of 0.0005 inch;
- K is a constant multiplier; and
- b is a calculatable constant which varies with the shape of the top of the float and the diameter of the tube.

When the commercially available "QBC" tube and float are used, the constant K will equal 3.411 and the constant b will equal −66.702. Other values of K and b can be readily ascertained by simple experimentation when tubes and floats of different sizes are used.

The aforesaid values of K and b were determined with blood samples from patients with hematocrit counts in the range of 30–48 (mean 39.4) which are counts normally seen by physicians. Blood samples with abnormally high of low hematocrit counts would indicate correspondingly lower or higher than normal plasma content, whereby appropriately modified K and b values might be required to obtain valid fibrinogen readings.

It is therefore an object of this invention to provide an improved procedure for measuring the fibrinogen content in a blood sample.

It is a further object of this invention to provide a procedure of the character described, wherein a simple sample centrifugation will produce an easily measurable precipitated fibrinogen layer in transparent sampling tube.

It is an additional object of this invention to provide a procedure of the character described, wherein the fibrinogen content of the blood sample is layered out as precipitated fibrinogen in the sampling tube separately from the remainder of the blood sample's formed elements.

It is yet another object of this invention to provide a procedure of the character described wherin the axial length of the precipitated fibrinogen layer in the sampling tube is proportional and convertable to a quantification of the fibrinogen content of the blood sample.

BRIEF DESCRIPTION OF THE DRAWING

These and other objects and advantages of the invention will become more readily apparent from the following detailed description of a preferred embodiment thereof when taken in conjunction with the accompanying drawing which is an elevational view of the sample tube with the float after the fibrinogen layer has been precipitated out on top of the float.

Referring now to the drawing, the tube is designated by the numeral 2, and may be a capillary or larger evacuated blood sampling tube. The tube 2 contains a float 4 which is made of plastic and which has a specific gravity that causes it to float in the centrifuged red blood cell layer. The top 8 of the tube 2 is open, and the bottom 6 is closed with a plastic cap 10. As previously noted, when the tube 2 is an evacuated blood sampling tube, it will not need the cap 10, but instead will have an integral closure wall 11 and a top closure plug 9. An anticoagulated blood sample is introduced into the tube 2 and centrifuged therein. This causes the red blood cells to layer out in a column 12 at the bottom of the tube 2, and the float 4 settles into and is buoyed up by the red blood cell column 12. Above the red cell layer 12, the white blood cell and platelet layer, or buffy coat, 14 settles out. The individual components of the buffy coat 14 will also layer out in separate bands as taught by the prior art. The plasma layer 16 is disposed above the buffy coat 14. It will be noted that the float 4 extends for a significant distance d above the buffy coat 14 in the plasma layer 16, whereby the top surface 5 of the float 4 is displaced away from the buffy coat 14.

After the initial blood cell readings, such as hematocrit, hemoglobin, differential white cell, and the like, are taken, the sample is heated to a temperature sufficient to precipitate the fibrinogen out of the plasma. Incubation of the sample at 56 degrees C for five minutes has been found to be operative. The sample is then once again centrifuged in the tube 2 for a time sufficient to agglomerate the precipitated fibrinogen into a band 18 at the top 5 of the float 4. The precipitated fibrinogen appears as a white band 18 which rests on the top surface 5 of the float 4. The fibrinogen layer 18 is thus separated from the buffy coat layer 14 for accurate measurement. The annular free space between the float 4 and the tube 2 must be kept small enough to prevent the precipitated fibrinogen from descending into the annular free space during the centrifugation step. The thickness of the free space for any particular tube and float combination for a known blood sample volume can be determined with conventional experimentation. When the "QBC" capillary tube and float combination of the type described in the aforesaid prior art is used, an annular free space having a thickness of 35 to 45 microns has been found to be operable.

The fibrinogen content is determined by measuring the axial dimension, or length, or the fibrinogen band 18 in the tube. This dimension is then converted mathmatically to a fibrinogen content reading. Thus, the length of the band is indicative of the quantity of fibrinogen in the blood sample.

It is essential that the fibrinogen band be separated from the buffy coat to greatly enhance the ability to accurately measure the extent of the height of the fibrinogen band.

In normal patients with normal buffy coat components, normal hematocrit counts, and a normal fibrinogen level, the unexpanded buffy coat band is about 10% of the height of the fibrinogen band. In patients with elevated buffy coat components and decreased fibrinogen concentrations, the buffy coat band can be greater in height than the fibrinogen band thereby leading to significant error if all or a part of the buffy coat is included in the measurement of the fibrinogen band.

It is understood that means, other than a float, for separating the fibrinogen layer from the formed blood components, can be used in performing the procedure described. For example: a gel layer of an appropriate specific gravity could be used to separate the fibrinogen layer from the formed buffy coat; or a quantity of plastic beads of an appropriate specific gravity could be used.

It is also understood that means other than heat may be used to precipitate the fibrinogen so that it may be measured in the described manner of this invention. For example, thrombin and calcium could be added to the blood sample to convert the fibrinogen to insoluble fibrin.

It will also be readily appreciated that the procedure described above will provide a simpler and more accurate quantification of the fibrinogen content of a blood sample. The use of the tube and float paraphenalia which is available from Becton Dickinson and Company under the trademark "QBC" makes the procedure usable in a physician's office whereby costly laboratory produces will be avoided. Additionally, test results will be quickly available to the physician and patient.

Since many changes and variations of disclosed embodiment of the invention may be made without departing from the inventive concept, it is not intended to limit the invention otherwise than as required by the appended claims.

What is claimed is:

1. An method for measuring the fibrinogen content of anticoagulated whole blood, said method comprising the steps of:
    a) providing a sample of the blood in a transparent tube containing a float spaced apart from said tube, said float and tube being sized relative to each other so as to prevent significant accumulation of fibrin or precipitated fibrinogen between the tube and float;
    b) centrifuging the blood sample to separate the formed and plasma components of the blood in the tube;
    c) converting the fibrinogen in the plasma to fibrin or to precipitated fibrinogen;
    d) recentrifuging the blood sample to form a layer of fibrin or precipitated fibrinogen in the plasma on one end of the float and spaced apart from the formed components of the blood in the tube; and
    e) measuring the length of the formed layer in the tube and converting the measured length of the layer to a quantified fibrinogen count.

2. The method of claim 1 wherein the float is of sufficient length to ensure that the formed layer will be spaced apart and readily discernible from any formed components in the blood sample.

3. The method of claim 1 wherein the conversion of fibrinogen to fibrin or precipitated fibrinogen is achieved by heating the blood sample in the tube.

4. The method of claim 1 wherein the conversion of formed layer length to fibrinogen count is accomplished by solving the equation:

$$F_q = KF_l + b$$

wherein:
   $F_q$ is the quantified fibrinogen count;
   $F_l$ is the measured length of the formed layer;
   K is a constant multiplier; and
   b is a constant which is a function of the shape of the end surface of the float and the diameter of the tube.

5. The method of claim 1 wherein the tube is a capillary tube.

6. The method of claim 1 wherein the tube is a preevacuated blood sampling tube.

7. A method for measuring the fibrinogen content of anticoagulated whole blood, said method comprising the steps of:
    a) providing a sample of the blood in a transparent tube containing a float spaced apart from said tube, said float and tube being sized relative to each other so as to prevent significant accumulation of precipitated fibrinogen between the tube and float;
    b) precipitating the fibrinogen in the blood sample;
    c) centrifuging the blood sample in the tube to cause the precipitated fibrinogen to layer out at an end of the float remote from the formed components of the blood sample; and
    d) converting the length of the precipitated fibrinogen layer to a fibrinogen count.

8. A method for quantifying the amount of a target component of a composite fluid material in a sample of the fluid material, said method comprising the steps of:
    a) providing a sample of the fluid material in transparent tube containing a float spaced apart from said tube, said float and tube being sized relative to each other so as to allow accumulation of some components in the sample in a free space between the tube and float, while preventing significant accumulation of said target component in said free space between the tube and float;
    b) centrifuging the sample in the tube to cause the target component to layer out in a band on top of the float and spaced apart from all other visible components of the fluid material; and
    c) measuring the axial length of the target component band, and converting the resultant measurement to a quanification of the target component in the sample.

* * * * *